(12) United States Patent
Streckfus et al.

(10) Patent No.: US 6,670,141 B2
(45) Date of Patent: *Dec. 30, 2003

(54) METHOD OF DIAGNOSING AND MONITORING MALIGNANT BREAST CARCINOMAS

(75) Inventors: Charles F. Streckfus, Brandon, MS (US); Lenora G. Bigler, Clinton, MS (US); James Tate Thigpen, Jackson, MS (US)

(73) Assignee: University of Mississippi Medical Center, Jackson, MS (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/962,477

(22) Filed: Sep. 25, 2001

(65) Prior Publication Data

US 2002/0015964 A1 Feb. 7, 2002

Related U.S. Application Data

(63) Continuation of application No. 09/259,993, filed on Mar. 1, 1999, now Pat. No. 6,294,349.

(51) Int. Cl.[7] ...................... G01N 33/574; G01N 33/53; G01N 33/567; G01N 33/566; G01N 33/48
(52) U.S. Cl. ......................... 435/7.23; 435/4; 435/7.1; 435/7.2; 435/7.21; 435/7.92; 435/7.93; 435/7.94; 435/7.95; 436/501; 436/63; 436/64
(58) Field of Search ...................... 435/7.1, 7.21, 435/7.23, 4, 7.2, 7.92, 7.93, 7.94, 7.95; 436/64, 501, 63

(56) References Cited

U.S. PATENT DOCUMENTS

| | | |
|---|---|---|
| 5,401,638 A | 3/1995 | Carney et al. |
| 5,512,657 A | 4/1996 | Van Aken et al. |
| 5,527,676 A | 6/1996 | Vogelstein et al. |
| 5,769,074 A | 6/1998 | Barnhill et al. |
| 5,840,889 A | 11/1998 | Cavalieri et al. |
| 5,858,365 A | 1/1999 | Faller |
| 5,858,683 A | 1/1999 | Keesee et al. |
| 6,294,349 B1 | 9/2001 | Streckfus et al. |

FOREIGN PATENT DOCUMENTS

| | | |
|---|---|---|
| WO | WO 91/02062 | 2/1991 |
| WO | WO 00/44403 | 8/2000 |

OTHER PUBLICATIONS

Streckfus, et al. "The Presence of CA 15–3, c–erB–2, Cathespin–D, EGFR, WAF1 and p53 in Saliva Among Women with Benign and Malignant Tumors." *Journal of Dental Research*, Jan. 30, 1998, p. 285, #1437, vol. 77, University of Mississippi Medical Center, Jackson, MS.

Dobrosielski–Vergona, K., Biology of University of Pittsburgh, Pittsburgh, Pennsylvania, PA, CRC Press, Inc., Boca Raton, FL.

Baum, B., "Age Changes in Salivary Glands and Salivary Secretion," Chapter 8: *Geriatric Dentistry—A Textbook of Oral Gerontology*, Edited by: Holm–Pedersen, P., and Loe, H., The C.V. Mosby Company, St. Louis; Washington, DC; Toronto.

Cook, D.I., et al., "Secretion by the Major Salivary Glands", *Chapter 26: Physiology of the Gastrointestinal Tract*, 1994, pp. 1061–1117, Third Edition, Raven Press, New York.

Sreenby, L., "The Salivary System", *Dept. of Oral Biology and Pathology*, pp. 128–131, State University of New York at Stony Brook, Stony Brook, New York, CRC Press, Inc., Boca Raton, Florida.

Chen, D., "Saliva and Serum CA 125 Assays for Detecting Malignant Ovarian Tumors", *Dept. of Obstetrics and Gynecology*, First Affiliated Hospital, Hunan Medical University, People's Republic of China, and the Dept. of Obstetrics and Gynecology, Yale University, School of Medicine, New Haven, Connecticut, Apr. 1990, pp. 701–703, vol. 75, No. 4.

Mandel, I., "Sialochemistry in Diseases and Clinical Situations Affecting Salivary Glands", *CRC Critical Reviews in Clinical Laboratory Sciences*, Sept. 1980, pp. 321–366, New York, New York.

*Primary Examiner*—Anthony C. Caputa
*Assistant Examiner*—Anne L. Holleran
(74) *Attorney, Agent, or Firm*—Reinhart Boerner Van Deuren s.c.

(57) ABSTRACT

A panel of biomarkers for the diagnosis and treatment of breast cancer was examined in the saliva of a cohort of 1) healthy women, 2) women with benign lesions of the breast and 3) women with diagnosed breast cancer. Recognized tumor markers c-erbB-2 (erb), cancer antigen 15-3 (CA 15-3), and tumor suppresser oncogene protein 53 (p53) were found in the saliva of all three groups of women. The levels of erb and CA 15-3 in the cancer patients evaluated, however, were significantly higher than the salivary levels of healthy controls and benign tumor patients. Conversely, pantropic p53 levels were higher in controls as compared to those women with breast cancer and those with benign tumors.

9 Claims, 7 Drawing Sheets

| MEDIUM | STATUS | CA 15-3 U/mg OF PROTEIN | erb UNITS/mg OF PROTEIN | p53 PMOL/mg OF PROTEIN | CD PMOL/mg OF PROTEIN | EGFR FMOL/mg OF PROTEIN | TOTAL PROTEIN mg/ml |
|---|---|---|---|---|---|---|---|
| SALIVA | CONTROLS (n=15) | 2.27 ± 1.45 | NOT DETECTABLE | 177.1 ± 61.3 | 26.29 ± 17.22 | 1.03 ± 0.69 | 1.25 ± 0.82 |
| SALIVA | BENIGN (n=8) | 2.22 ± 1.95 | NOT DETECTABLE | 180.7 ± 70.78 | 40.57 ± 13.05 | 0.37 ± 0.31 | 1.44 ± 0.92 |
| SALIVA | Ca IN SITU (n=12) | 5.26 ± 4.12* | 51.3 ± 43.96‡ | 134.6 ± 63.8 | 34.5 ± 27.95 | 0.92 ± 0.8 | 1.71 ± 0.79 |
| SERUM | CONTROLS (n=15) | 16.17 ± 4.64 | NOT DETECTABLE | 14.2 ± 7.9 | 67.5 ± 35.61 | 8.5 ± 8.45 | 24.54 ± 13.86 |
| SERUM | BENIGN (n=8) | 15.25 ± 5.04 | NOT DETECTABLE | 14.63 ± 8.8 | 45.0 ± 20.98 | 3.52 ± 1.89 | 27.33 ± 14.23 |
| SERUM | Ca IN SITU (n=12) | 24.68 ± 10.9*# | 81.68 ± 111.77# | 8.9 ± 7.7 | 63.17 ± 38.4 | 5.63 ± 3.10 | 29.23 ± 11.08 |

FIG. 1

METHOD OF DIAGNOSING AND MONITORING MALIGNANT BREAST CARCINOMAS

This application is a continuation application of application Ser. No. 09/259,993 filed Mar. 1, 1999 now U.S. Pat. No. 6,294,349 and claims priority benefit therefrom.

BACKGROUND OF THE INVENTION

This invention relates generally to the use of salivary biomarkers to diagnose breast cancer and, more particularly, to diagnostically differentiate between women with carcinoma of the breast, women with benign tumors, and healthy controls.

Breast cancer is the second leading cause of death among women in the United States. Approximately 1 woman in every 10 will develop breast cancer in her lifetime. Recent statistics estimate that 44,000 women will die of breast cancer, while 150,000 new female cases of breast cancer will be diagnosed in the next year.

It has been shown that screening for breast cancer can reduce breast cancer mortality. Among women aged 50 and older, studies have demonstrated a 20% to 40% reduction in breast cancer mortality for women screened by mammography and clinical breast examination. However, among women between 40 to 49 years of age, the mortality rate is reduced only 13% to 23%. These results suggest that further methods of screening could potentially reduce the mortality in the younger age group of women.

While physical examination and mammography are useful screening procedures for the early detection of breast cancer, they can produce a substantial percentage of false positive and false negative results especially in women with dense parenchymal breast tissue. For example, the probability of having a false negative mammographic examination is 20% to 25% among women between 40 to 49 years of age and 10% among women 50 to 69 years of age. Consequently, screening will result in a number of negative biopsy results yielding a high percentage of false positives. There is also a demonstrated lack of sensitivity in detecting cancerous lesions in younger women yielding a significant percentage of false negatives.

There has also been a clear need for added modalities of screening to help diagnose cancer in younger women. Increased technology in the field of mammography has allowed more reliable detection of small lesions of the breast; while, researchers in the field of breast cancer continue to seek additional adjunct diagnostic procedures to further enhance cancer screening and, thereby, to reduce mortality rates.

During the past three decades, cancer researchers have made extensive use of immunohistochemistry to detect expression of specific biomarkers that may be used as adjunct diagnostic procedures in the diagnosis of certain tumors. (Grizzle WE. Biomarkers-The New Frontier in the Pathology of Invasive and Preinvasive Neoplasias. Biotechnic and Histochemistry, 72(2):59–61, 1997; Grizzle W E, Myers R B, Manne U. The Use of Biomarker Expression to Characterize Neoplastic Processes. Biotechnic and Histochemistry, 72(2):96–104, 1997.) Tumor markers such as c-erbB-2 (erb) and Cathespin-D (CD) have been assayed in tissue and shown to correlate with aggressive lesions. The majority of the investigations performed have used these markers in tissues and serum.

With respect to specific cancer antigens in saliva, Chien found that saliva contained CA 125, a glycoprotein complex that is a recognized or accepted tumor marker for epithelial ovarian cancer. (Chien D X, Schwartz P E, CA 125 Assays for Detecting Malignant Ovarian Tumors. Obstetrics and Gynecology, 75(4):701–704, 1990.) In comparing salivary CA 125 concentrations among healthy controls, women with benign lesions, and those with ovarian cancer, Chien found a significantly elevated CA 125 concentration among the ovarian cancer group as compared to the nonmalignant controls. Boyle detected and identified tumor-specific mutations using radio-labeled oligonucleotide in preoperative salivary samples of individuals suffering from head and neck squamous cell carcinoma. These findings were demonstrative in 71% of the patients studied. (Boyle J O, Mao L, Brennan J A, Koch W M, Eisele D W, Saunders J R, Sidransky D. Gene Mutations in Saliva as Molecular Markers for Head and Neck Squamous Cell Carcinomas. Am J Surgery, 168(5):429–32, 1994.)

SUMMARY OF THE INVENTION

However, such antigens are not diagnostic for breast cancer, and the aforementioned tumor biomarkers (e.g., CA 125, erb and CD) have not been tested for their presence in saliva. While the diagnostic methods of the prior art have generally progressed, such innovations have not been extended to all areas of diagnosis. There is a need for a method to more fully utilize recent technological advances and apply them to the detection and treatment of breast carcinomas.

Accordingly, it is an object of the present invention to use saliva as a diagnostic medium and/or as part of a noninvasive protocol for the detection and differential diagnosis of breast carcinomas, thereby overcoming various deficiencies and shortcomings of the prior art, including those outlined above.

It can be another object of the present invention to identify one or more biomarkers present in saliva, as having diagnostic value and/or as can be used in post-treatment monitoring or therapy. Likewise, it can be another object to provide one or more biomarkers as part of a diagnostic panel for the initial detection, follow-up screening for detection, reoccurrence of breast cancer in women, response to chemotherapy and/or surgical treatment of the disease state.

It would be understood by those skilled in the art that one or more aspects of this invention can meet certain objectives, while one or more other aspects can meet certain other objectives. Each objective may not apply equally, in all instances, to every aspect of the present invention. As such, these objectives—in light of the prior art regarding diagnosis of breast cancer—can be viewed in the alternative with respect to any one aspect of the present invention.

Other objects, features, benefits and advantages of the present invention will be apparent from this summary and the following inventive examples, and will be readily apparent to those skilled in the art having knowledge of the nature and detection of cancer biomarkers and their use in the diagnosis of corresponding disease states. Such objects, features, benefits and advantages will be apparent from the above as taken in conjunction with the accompanying examples, tables, data and all reasonable inferences to be drawn therefrom.

In part, the present invention is a method of using a salivary biomarker to differentially diagnose and/or detect reoccurrence of breast carcinoma. The method includes (1) using a human saliva specimen to provide a salivary biomarker for that individual and diagnostic for carcinoma of the breast, (2) comparing the individual biomarker with a biomarker reference, and (3) differentially identifying the diagnosis for the individual as indicated by the biomarker comparison. The biomarker reference can be made up of a panel of constituents and can be developed using malignant tumor, benign tumor and control group populations. Each referenced biomarker constituent can have associated with it a range of values comparable to a corresponding individual biomarker.

In preferred embodiments, the individual biomarker is one constituent of a biomarker panel, and the reference panel includes one or more biomarkers identified as having diagnostic value. Such biomarkers can include cancer antigen 15-3, tumor suppressor oncogene protein 53 and oncogene c-erbB-2. In highly preferred embodiments of the inventive method, the presence of oncogene c-erbB-2 and/or an increased expression of protein identifies an individual as having a malignant carcinoma.

Each individual biomarker constituent can be associated with a concentration value, for comparison with a corresponding reference constituent. In one embodiment of the present invention, the concentration of cancer antigen 15-3 for an individual having a malignant breast tumor is at least about 100 percent higher than such a concentration for an individual having a benign tumor. Likewise, in a preferred methodology, the concentration of oncogene protein 53 for an individual having a malignant breast tumor is at least about 25 percent lower than an individual having a benign tumor. Such differential identifications can be used alone or in conjunction with one or more primary diagnostic methods for the testing and detection of breast carcinomas.

In part, the present invention is a post-operative method of monitoring tumor growth. The method includes (1) providing an individual post-operative to the removal of a malignant tumor, (2) using a saliva specimen from that individual to develop a post-operative biomarker panel, (3) comparing the post-operative biomarker panel with a pre-operative biomarker reference panel for the individual, and (4) determining the presence of malignancy by monitoring at least one constituent of the respective biomarker panels.

Typically, and in preferred embodiments of this method, post-operative chemotherapy is administered to the individual. The chemotherapy can include but is not limited to a therapeutic regimen of cyclophosphamide, methotrexate and fluorouracil. In preferred embodiments, both biomarker panels include a c-erbB-2 constituent, the post-operative detection of which indicates tumor reoccurrence. Alternatively, both biomarker panels can include tumor suppressor oncogene protein 53 as a constituent, the post-operative absence of which indicates tumor inhibition.

In part, the present invention is a method of using the concentration of an endogenously encoded protein to diagnose carcinoma of the breast. The method includes (1) using a saliva specimen from an individual to provide a protein biomarker diagnostic for carcinoma of the breast, (2) comparing the individual protein biomarker with a reference protein, and (3) determining an elevated concentration of the individual protein biomarker over the referenced protein to diagnose the individual. In preferred embodiments, the biomarker protein is one constituent of a biomarker panel. Likewise, the reference protein can be one constituent of a reference panel. Regardless, any such protein can be developed as a reference using malignant tumor, benign tumor and control group populations. In highly preferred embodiments, the individual protein biomarker is cancer antigen 15-3 or, alternatively, an expression of oncogene c-erbB-2.

The biomarkers and related inventive method can be used for detecting breast carcinoma and provide for an economical and logistical adjunct diagnostic test for mammography. Furthermore, these salivary markers can also, in conjunction with physician and self breast examination, help to reduce morbidity and mortality rates for breast cancer and thereby reduce overall national health care expenditures.

BRIEF DESCRIPTION OF THE DRAWINGS

FIG. 1 is a compilation of mean values for healthy controls, individuals having benign lesions and carcinomas in situ (Ca in Situ), comparing saliva and serum media: ‡=erb control (saliva)<erb cancer group (saliva) one way sample test t-test (mean vs constant): t-value=14.31, p>0.0001; ‡‡=erb control (serum)<erb cancer group (serum) one way sample t-test (mean vs constant) t-value=10.33, p<0.0001; #=CA 15-3 control & benign (saliva)<CA 15-3 cancer group (saliva) Anova p<0.05; and ##=CA 15-3 control & benign (serum)<CA 15-3 cancer group (serum) Anova p<0.01.

EXAMPLES OF THE INVENTION

Figure 2:
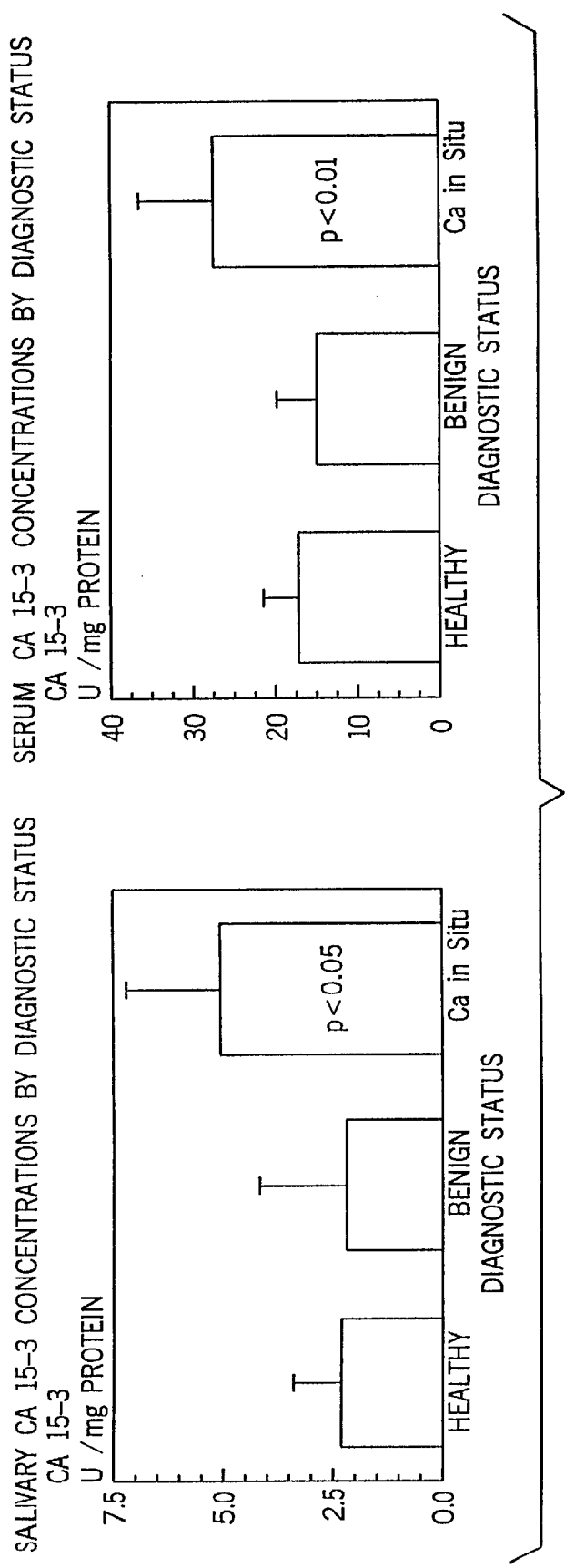
FIG. 2 is a tabular comparison of salivary and serum concentrations (U/mg protein) of CA 15-3, by diagnostic status.

The following non-limiting examples and data illustrate various aspects and features relating to the method(s) of the present invention, including the surprising and unexpected results obtained thereby.

With respect to the following examples and data, the subject population consisted of 21 women from the general population (controls) and the University of Mississippi Medical Center (UMMC), Department of Oncology and Surgery Clinics (tumor patients). Individuals with a breast mass were referred to UMMC from the surrounding community for evaluation. Each patient was given a thorough physical examination and evaluated for carcinoma of the breast. Saliva and serum specimens were collected from each women at the initial visit at the clinic and prior to receiving any treatment. Final pathologic diagnostic evaluations later revealed whether the individual had a benign tumor, or carcinoma of the breast (in situ). Investigators were initially blind with respect to diagnostic outcome of the subjects until a final diagnosis was rendered by the pathologist and the patient referred for further treatment. The subjects were racially mixed and ranged in age from 30 to 80 years.

False positive results were eliminated. It was initially envisioned that the present methodology might provide false positives due to extraneous physiological and environmental factors such as estrogen levels and smoking, respectively. However, such factors have been eliminated as providing false positive results. Race, age, menopausal status, medication usage and health status were also eliminated as factors producing false positive results.

Assays were determined as indicated using the referenced commercial kits and associated reagents, procedures and/or techniques. Kits from Triton Diagnostics are no longer available. Kits from CIS bio international are particularly useful and provide enhanced sensitivity, especially with regard to the erb marker.

EXAMPLE 1

Statistical Analysis. Statistical analysis were performed using the SPSS statistical software package. A descriptive analysis was made comparing mean marker values for the controls, those with benign tumors, and carcinoma of the breast.

A one-way analysis of variance for unbalanced data, the general linear models procedure, was used to compare the mean values for the group with breast carcinoma with a non cancer groups. The polynomials formulated using the general linear models procedure are easy to interpret and are appropriate for all sample sizes including those too small to sustain an appropriate multivariate analysis. The Tukey post-hoc analysis was used for significant linear models. Considering that erb was undetected among controls and benign lesions for both saliva and serum, a one way sample t-test was performed. Due to the small sample size, issues concerning the specificity and sensitivity of the panel of markers were not addressed, but will be investigated in subsequent studies.

EXAMPLE 2

Specimen Collection. Stimulated whole saliva specimens were collected for a 5 minute period using a cube of paraffin as a stimulant (Navasesh, 1982)[17] Salivary flow rates were determined gravimetrically. All specimens were collected in the morning thereby controlling for any possible effects that circadian rhythm may produce in marker concentration. Samples can be frozen for future analysis. Blood was also drawn at the time of saliva collection by a phlebotomist. None of the participants exhibited cancerous or precancerous lesions in the oral cavity at the time the specimens were collected.

The frozen saliva samples were thawed and centrifuged at 500–1500G for 20 min to precipitate cells and mucin in order to extract the bio-marker proteins. The clear saliva extract and the serum from the blood specimens were analyzed for total protein and the panel of biomarkers.

EXAMPLE 3

Total Protein. A calorimetric assay for measuring total protein concentration, based on the color change of Coomassie brilliant blue G-250 dye in response to various concentrations of proteins, was used (Bio-Rad Kit). Specimens were read on a spectrophotometer and absorbance measured at 595 nm. Total protein concentration of the samples was determined from a standard curve constructed with bovine gamma globulin standards.

EXAMPLE 4

CA 15-3. CA 15-3 assays were determined by using EIA kits (CIS bio international). The CA 15-3 assay is a two-site solid phase enzyme immunoassay. The molecules of CA 15-3 are "sandwiched" between two monoclonal antibodies, the first one attached to the ELSA solid phase and the second one linked to the horseradish peroxidase (enzymatic conjugate). After washing, the enzymatic reaction develops a color proportional to the amount of CA 15-3 present in the assay. Absorbances are read at 490 nm using a spectrophotometer and concentrations are calculated from standard curves constructed from known concentrations of the ligand. The CA 15-3 assay is designed to assay serum specimens. Saliva supernatants were substituted in place of the serum for salivary CA 15-3 determinations. The antibodies used in the test do not present cross-reaction with other known tumor markers (CEA, CA 19-9, CA 125) and the salivary concentrations are substantially above the lower limit of detection for the assay. CA 15-3 concentrations were expressed as units/mg of protein.

EXAMPLE 5 erb and pantropic p53. erb and pantropic p53 assays were determined using ELISA kits (Oncogene Research, Co.). In this study serum and the salivary supernatant were substituted in place of the tissue extracts as assay specimens. A colormetric evaluation of the level of binding was performed and the intensity of the color formed by the enzymatic reaction is proportional to the target protein present. Absorbances were read at 490 nm in a microplate spectrophotometer and ligand concentrations calculated from standard curves. erb and p53 data were expressed as units/mg of protein and pmol/mg of protein, respectively. The antibodies used in the test do not present cross-reaction with other known tumor markers and the salivary concentrations are substantially above the lower limit of detection for the assay.

EXAMPLE 6

Cathepsin-D Assay. Salivary and serum CD concentrations were determined using enzyme immunoassay (EIA) kit (Triton Diagnostics, Inc.). A monoclonal antibody and a rabbit polyclonal antibody both specific for CD were simultaneously incubated with both the saliva and serum specimens. During the incubation, the CD present in the saliva and serum specimens was bound by the two anti-CD antibodies. The monoclonal antibody is conjugated to biotin causing the formed antigen-antibody complex to be bound onto the streptavidin-coated tube. Unbound materials were removed by washing the tubes. In the second incubation, an anti-rabbit antibody conjugated with horseradish peroxidase was added to the tube. The conjugate was then bound to the complex. Unbound complex was removed by a second washing. The tubes were then incubated with a TMB substrate solution in order to develop a color. Phosphoric acid was then added to stop the enzymatic reaction. The intensity of the color that was developed was determined using a spectrophotometer set at 450 nm. Specimen values were determined from the curve which resulted by plotting the absorbance values of the controls against the known concentrations (pmol/mg of protein).

EXAMPLE 7

Epidermal Growth Factor Receptor. EGFR assays were determined using EIA kits (Triton Diagnostics, Inc.). The anti-EGFR conjugate was incubated with the saliva and serum specimens. During the incubation the EGFR protein becomes bound by the anti-EGFR conjugate. One of the monoclonal antibodies is conjugated to horse radish peroxidase. During the second incubation the resulting immune complexes become bound onto a coated polystyrene tube by a "linking solution". Unbound substrates were then washed by decanting. The tubes were then incubated with a TMB substrate solution in order to develop a color. Phosphoric acid was then added to stop the enzymatic reaction. The intensity of the color that was developed was determined using a spectrophotometer set at 450 nm. Specimen values were determined from the curve which resulted by plotting the absorbance values of the controls against the known concentrations(fmol/mg of protein).

For all their power, immunoassays are subject to many kinds of interference. The investigators performed several test laboratory tests to control for these problems. With respect to ligand recovery, the investigators were able to establish the amount of marker (ligand) recovered from saliva and serum samples. Five saliva and serum specimens with known amounts of marker were serially diluted. The dilutions were assayed for all three markers. The data were plotted against the expected values to determine the linearity of dilution. The slopes of both the dose response curve and the standard curve were not significantly different from each other and the intercepts were not significantly different from zero. During the assaying of the specimens, the investigators employed the use of appropriate positive and negative controls for all marker assays. When performing the assays, some test specimens contained primary antibodies preincubated with excess ligand to control for false positives. In addition, test specimens were preincubated with excess free primary antibody to determine if the signal had been eliminated. These extra tests provided additional quality control during the course of specimen analyses. When assayed, all specimens were run in triplicate.

The control group consisted of 15 women (age 42.4), the benign tumor group consisted of 8 women (age 45.3), and the cancer group consisted of 12 women (age 49.0). The subjects diagnosed with benign lesions consisted of women with fibroadenomas (n=4), lipomas (n=1), and fibromas (n=3). The women with breast cancer were diagnosed with lobular carcinoma (n=1), infiltrating ductal carcinoma (n=9), and ductal carcinoma in situ (n=2). All of the subjects with carcinoma of the breast were node negative and without evidence of metastases. Five of the cancer subjects among the cancer group were edentulous while only two among the non-cancer group were edentulous. All other subjects were dentate. The mean values for the three groups are shown in FIG. 1 and illustrated graphically in FIGS. 2–7.

As shown in FIGS. 1 and 2, the mean values for CA 15-3 among the controls and benign lesions group were approximately 45%–50% lower than the mean value for the cancer group. This was statistically significant at the $p<0.05$ level for saliva and $p<0.01$ level for serum.

Figure 3:
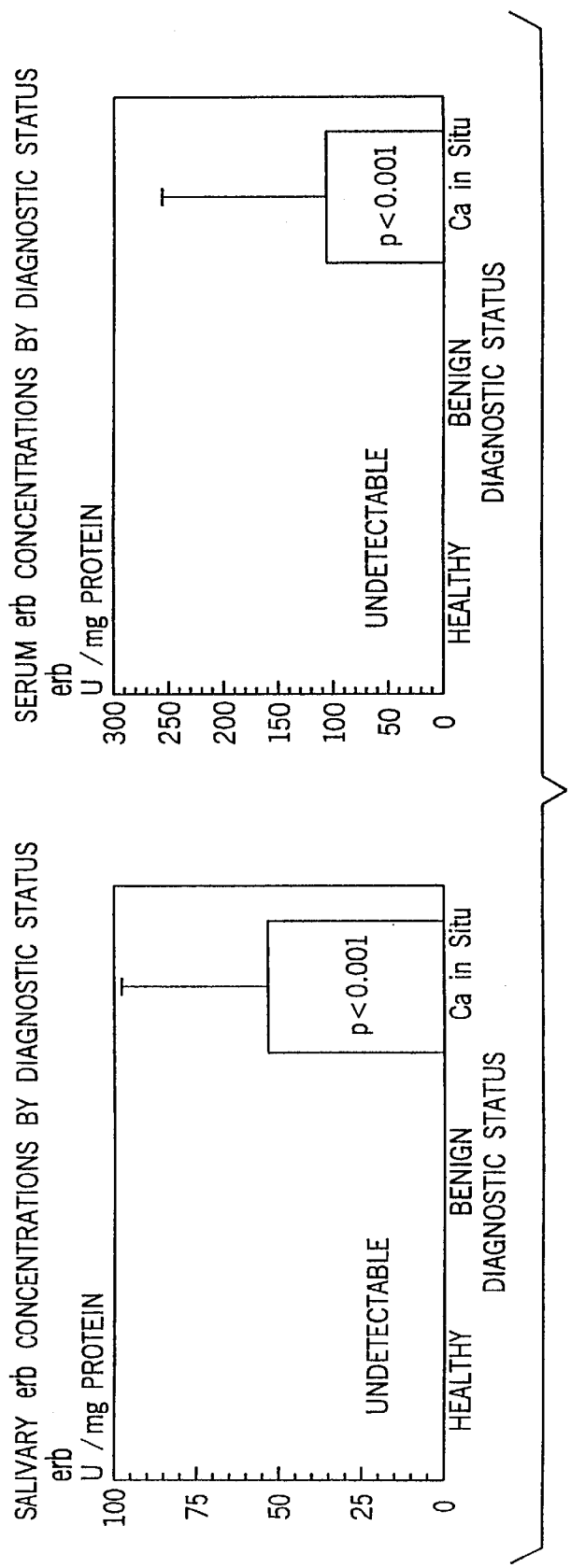
FIG. 3 is a tabular comparison of salivary and serum concentrations (U/mg protein) of erb, by diagnostic status.
Figure 4:
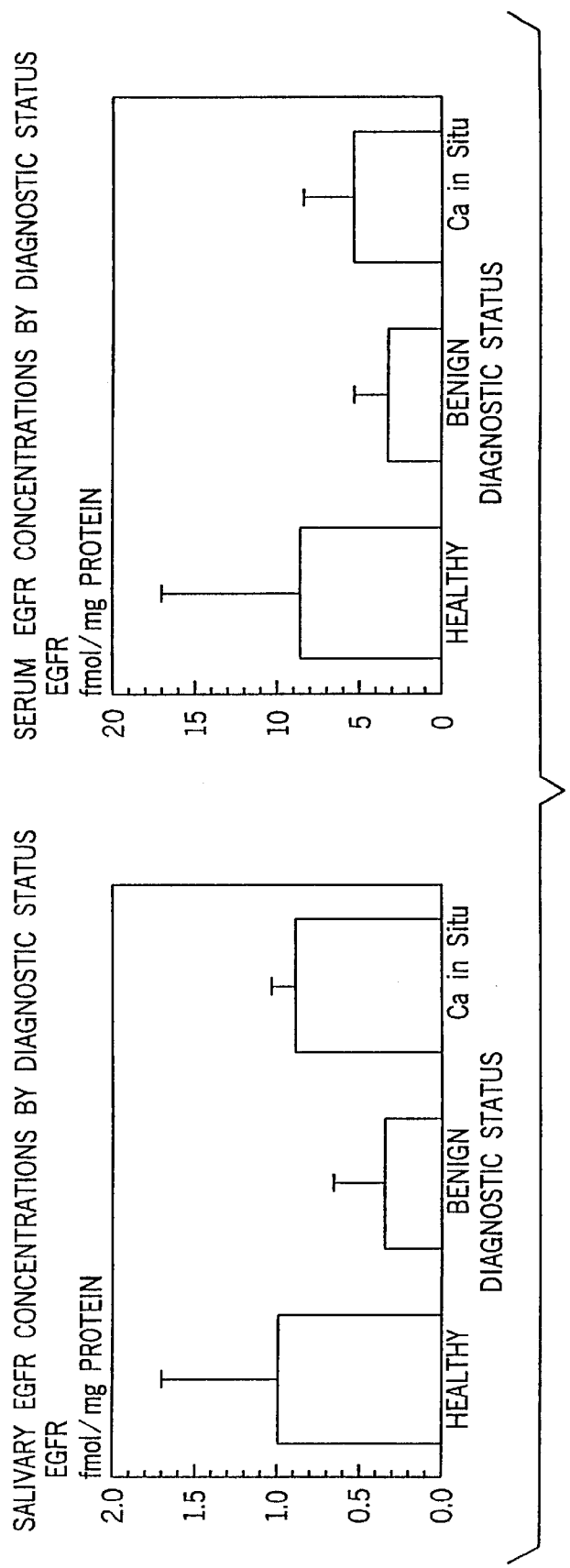
FIG. 4 is a tabular comparison of salivary and serum concentrations (fmol/mg protein) of EGFR, by diagnostic status.
Figure 5:
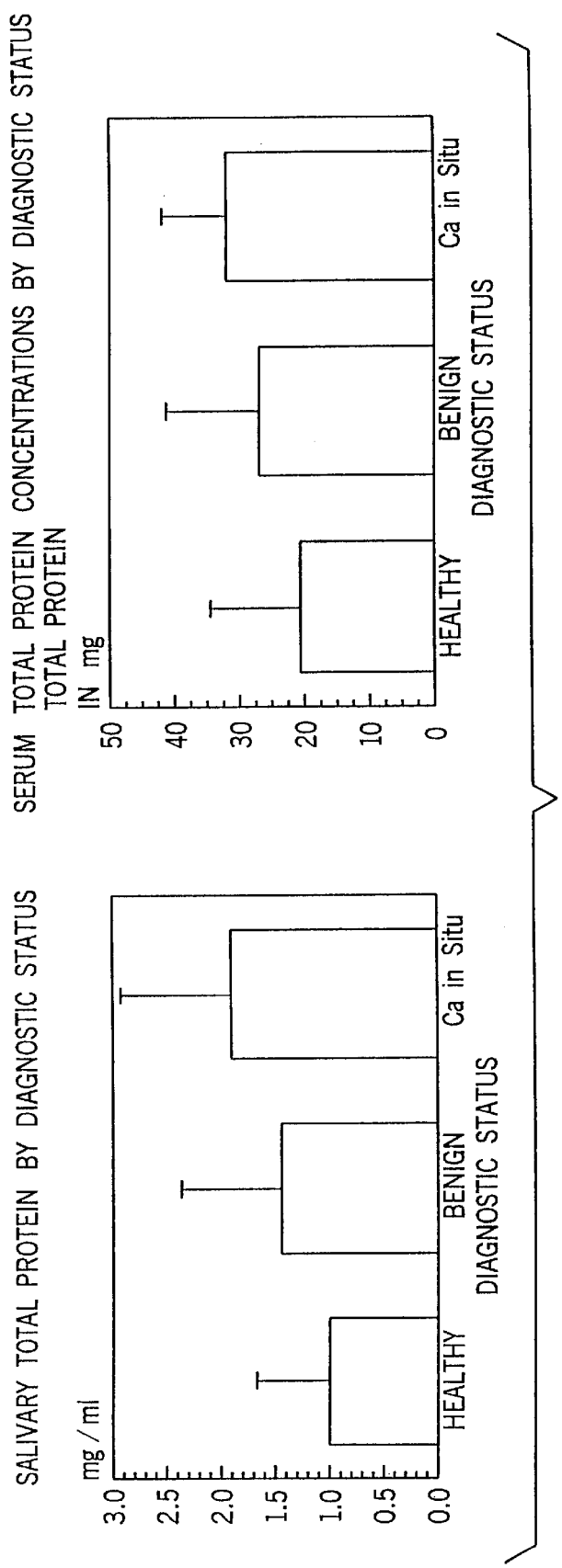
FIG. 5 is a tabular comparison of salivary and serum total protein concentrations (mg/ml), by diagnostic status.

Referring to FIGS. 1 and 3, erb was not detected in the saliva or the serum of the controls or benign lesions group. Conversely, the carcinoma group exhibited the presence of erb and the t-test showed significantly higher concentrations ($p<0.001$).

Figure 6:
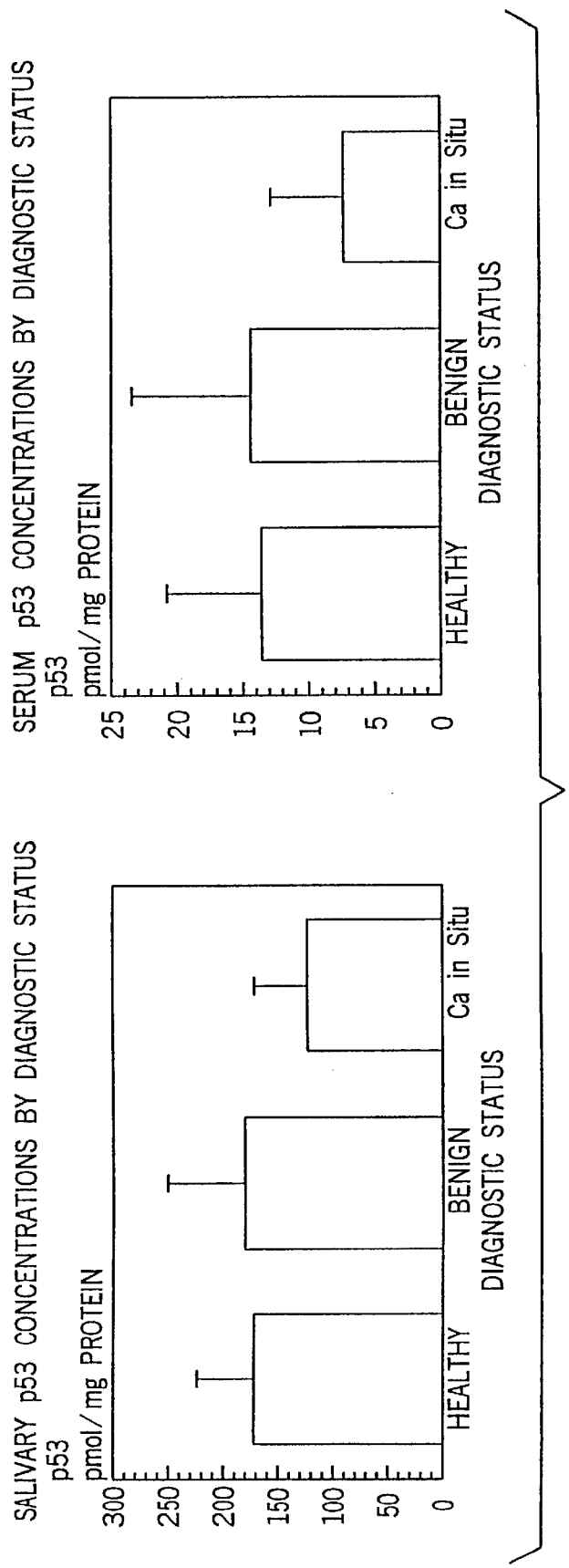
FIG. 6 is a tabular comparison of salivary and serum concentrations (pmol/mg protein) of p53, by diagnostic status.
Figure 7:
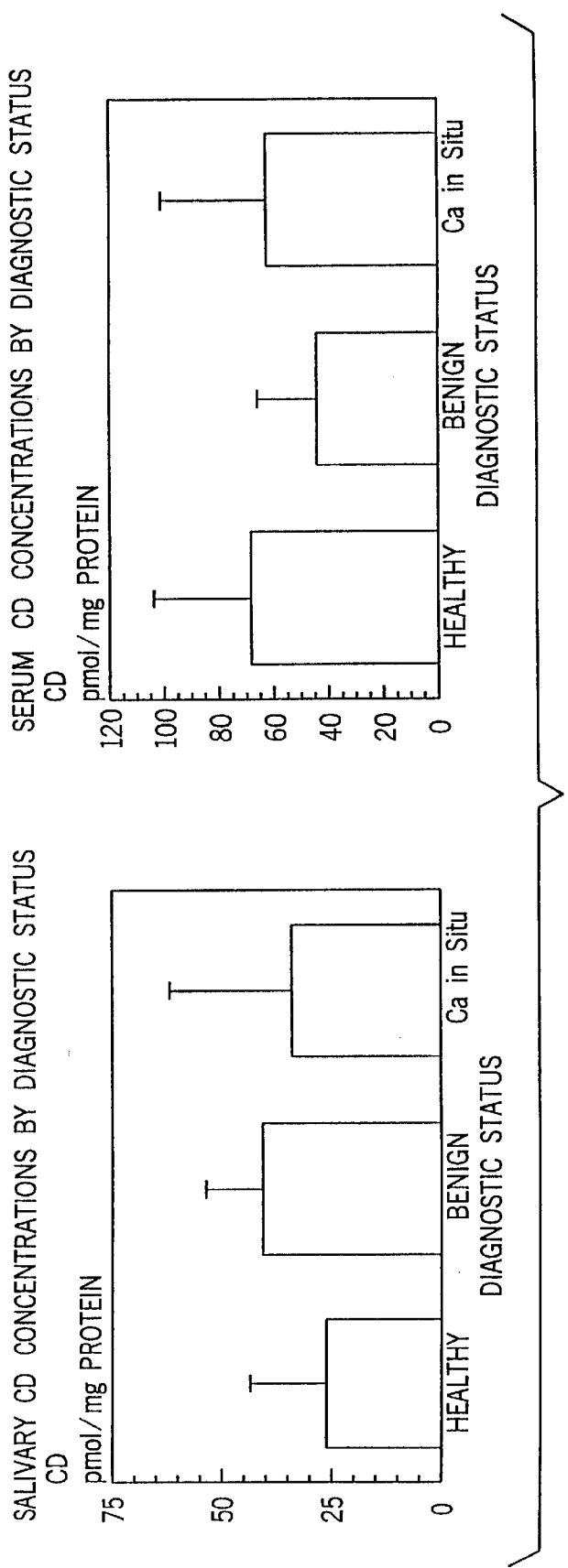
FIG. 7 is a tabular comparison of salivary and serum concentrations (pmol/mg protein) of CD, by diagnostic status.

Additionally, p53 levels were approximately 25% higher among the controls and the benign lesion groups as compared to the cancer group (FIGS. 1 and 6.) The investigators expected higher p53 values among the controls as compared to those women with breast cancer in so far as p53 mutation reflects the inability of the oncogene to render tumor suppression. As shown in the accompanying figures, saliva and serum levels of CD and EGFR did not appear to be as tumor specific as CA 153, erb and p53 when compared across the three groups of women.

EXAMPLE 8a

With respect to the presence of the panel of markers in saliva, several technical issues were also addressed. One such issue was to determine if cells from the oral epithelium may possibly contribute to marker levels found in the saliva. To address this, salivary specimens were centrifuged and the supernatant separated from the pellet. A sample from the supernatant was placed on a glass slide, stained and microscopically examined for the presence of cells. The examination disclosed the absence of cells in the supernatant. Next, the pellet was resuspended in phosphate buffered saline. Both the supernatant and the resuspended pellet were analyzed for the presence of the biomarkers. The results showed biomarker levels in the supernatant, but an absence of biomarkers in the resuspended pellet, indicating the biomarkers originate in the saliva and that there are no biomarker contributions from the cells.

EXAMPLE 8b

A second experiment was performed using secretory IgA (sIgA) as a control protein to compare individuals with and without carcinoma of the breast. The predominant immunoglobulin in saliva is sIgA. It is derived from salivary glands with the parotid gland being the principal producing gland. The antibody is synthesized as IgA dimers by immunocytes present in the major and minor salivary glands. Because of its ability to attenuate pathogenic assault, sIgA is consider to be the oral cavity's first line of defense. This salivary protein has no relationship with carcinoma of the breast and was selected as a control protein. Using ELISA methodology, sIgAs were detected in the saliva from both the cancer and the non-cancer groups. The results of this test showed no significant differences among those individuals with ($\bar{x}$ 11.7 ng/ml) and without cancer ($\bar{x}$ 14.3 ng/ml), indicating that the only proteins which appear to be elevated are those markers associated with carcinoma of the breast.

EXAMPLE 8c

A third experiment was performed to determine the effects of oral health on the marker levels. A small number of individuals with periodontal disease was compared to healthy controls and several edentulous subjects. The results showed no significant difference in marker levels among those with periodontal disease, those who were orally healthy and those who were edentulous.

EXAMPLE 8d

A fourth experiment was conducted to determine the effects of the estrous cycle on salivary marker levels. Two healthy women with regular menses had saliva specimens collected daily from the beginning of their menstrual cycle to its end. The results showed no major fluctuations of salivary marker concentrations occurring during the menstrual cycle. Marker concentrations were relatively consistent over the 30 day period suggesting minimal individual variability (data not shown).

EXAMPLE 8e

Another experiment was conducted to determine the origin of the salivary gland constituents. Parotid, submandibular, sublingual and minor gland secretions were collected. The results of this experiment indicate that these markers are primarily secreted by the parotid gland. Parotid gland secretions were found to be many times higher than the submandibular, and sublingual concentrations. Minor gland contributions were barely detectable. Additionally, marker concentrations appear to be flow rate independent.

As shown above, detectable levels of the breast tumor markers CA 15-3, erb, EGFR, CD, and p53 were present in the saliva and serum of women with malignant breast lesions. These markers are also detectable in the saliva and serum of women with benign breast lesions and completely healthy individuals. The results also indicate lower levels of CA 15-3, erb, in noncancer individuals as compared to those with breast carcinoma (FIG. 1). The reverse was true with respect to p53.

Several potential confounding factors were also considered and resolved. Accordingly, it was determined that: 1) the cells from the oral epithelium did not contribute to the marker levels, 2) using sIgA as a control protein, the only proteins which are elevated are those markers associated with carcinoma of the breast, 3) the presence of periodontal disease has no effect on marker levels, 4) the estrous cycle had no effect on salivary marker levels, 5) the markers are secreted primarily from the parotid gland and 6) are flow rate independent.

As a diagnostic medium, saliva has several biochemical advantages. Saliva is a clear, colorless liquid while serum may become milky when lipemic, red when blood cells are hemolyzed due trauma and icteric in the presence of liver disease. These color fluctuations in normal and disease altered serum can affect calorimetric assays such as ELISA, make it difficult to produce a consistent blank and interfere with the true values of the serum assay when compared to the consistent clarity of the assay standards. Since serum possesses more proteins than saliva assaying trace amounts of other factors (i.e., oncogenes, etc.), may result in a greater risk of non-specific interference and a greater chance for hydrostatic (and other) interactions between the factors and the abundant serum proteins.

From a logistical perspective, the collection of saliva is safe (i.e., no needle punctures), non-invasive and relatively simple, and may be collected repeatedly without discomfort to the patient.

The diagnostic benefits arising from the present invention could include the overall management of breast cancer in women. The diagnosis of breast cancer at an earlier stage allows a woman more choice in selection of various treatment options. A saliva based test would be useful in the postoperative management of cancer patients. Following tumor removal, an expected decrease in marker concentration should follow and eventually plateau to within a normal level indicating that the patient is free of disease. In contrast, a persistently high level of salivary markers may be indicative of tumor recurrence or persistence. Saliva could also be a cost effective method for monitoring the effectiveness of chemotherapy. Individuals should experience decreases in marker concentrations if the treatment regimen is effective.

While the principals of this invention have been described in connection with specific embodiments, it should be understood clearly that these descriptions, along with the chosen tables and data therein, are made only by way of example and are not intended to limit the scope of this invention, in any manner. For example, and without limitation, the methodology described herein can be extended to the diagnosis and monitoring of gall bladder, colon, rectal, pancreatic and oral cancers. Other advantages and features of this invention will become apparent from the following claims, with the scope thereof determined by a reasonable equivalents, as understood by those skilled in the art.

What is claimed is:

1. A method of using salivary secretion to diagnose carcinoma of the breast in a human test subject, said method comprising:
    providing a saliva specimen from a human test subject, said specimen including a salivary secretion portion from the saliva glands of the test subject;
    analyzing said salivary secretion portion for the presence of a biomarker for breast carcinoma in said salivary secretion, said presence having an associated salivary concentration, said biomarker selected from the group consisting of cancer antigen 15-3, tumor suppressor oncogene protein 53, oncogene c-erbB-2 and combinations thereof; and
    using said salivary secretion concentration to diagnose said human subject.

2. The method of claim 1 wherein said biomarker is an expression of oncogene c-erbB-2.

3. The method of claim 1 wherein said diagnosis differentiates a malignant tumor from a benign tumor.

4. The method of claim 1 wherein said diagnosis is an adjunct to a primary diagnostic test for carcinoma of the breast.

5. The method of claim 1 further including mammography.

6. A post-treatment method of monitoring the inhibition of breast tumor growth, said method comprising:
    providing a human test subject, said subject post-treatment for a malignant tumor, said treatment selected from the group of treatments consisting of surgical operation, chemotherapy and combinations thereof;
    providing a salivary secretion specimen from said subject to develop a post-treatment salivary secretion biomarker panel, said panel having constituents selected from the group consisting of cancer antigen 15-3, tumor suppressor oncogene protein 53, oncogene c-erbB-2 and combinations thereof;
    using said post-treatment and salivary secretion biomarker panel to compare with a pre-treatment reference panel for said subject; and
    determining the post-treatment inhibition of breast malignancy by monitoring at least one said salivary secretion biomarker.

7. The method of claim 6 wherein a chemotherapeutic regimen is administered post-operatively to said subject.

8. The method of claim 6 wherein said pre-treatment and said post-treatment panels include a c-erbB-2 biomarker constituent.

9. The method of claim 6 wherein said pre-treatment and said post-treatment panels include a tumor suppressor oncogene protein 53 biomarker constituent.

* * * * *